United States Patent [19]

Howard et al.

[11] Patent Number: 5,266,477

[45] Date of Patent: Nov. 30, 1993

[54] MONOCLONAL ANTIBODIES WHICH DIFFERENTIATE BETWEEN NATIVE AND MODIFIED PORCINE SOMATOTROPINS

[75] Inventors: David K. Howard, Terre Haute; Anne M. Gill, Indianapolis, both of Ind.

[73] Assignee: Pitman-Moore, Inc., Mundelein, Ill.

[21] Appl. No.: 474,150

[22] Filed: Feb. 2, 1990

[51] Int. Cl.$^5$ .......................... C12N 5/20; C07K 15/28
[52] U.S. Cl. .............................. 435/240.27; 435/70.21; 435/172.2; 530/388.24; 530/389.2; 530/399
[58] Field of Search .................. 530/387–389, 530/399, 388.24, 389.2; 435/70.21, 172.2, 240.27; 424/85.8, 88

[56] References Cited

U.S. PATENT DOCUMENTS

| | | | |
|---|---|---|---|
| 4,332,717 | 6/1982 | Kanaoka et al. | 260/112 R |
| 4,431,739 | 2/1984 | Riggs | 435/253 |
| 4,443,539 | 4/1984 | Fraser et al. | 435/68.1 |
| 4,487,829 | 12/1984 | Sharp et al. | 435/7.92 |
| 4,604,359 | 8/1986 | Goeddel et al. | 435/253 |
| 4,623,621 | 11/1986 | Pestka | 435/7.92 |
| 4,864,019 | 9/1989 | Vale et al. | 530/387 |

FOREIGN PATENT DOCUMENTS 0103395  3/1984  European Pat. Off. .
0104920  4/1984  European Pat. Off. .

OTHER PUBLICATIONS

Couraud, Journal of Immunology, 136, "Structural Analysis of the Epitopes Recognized by Microclonal Antibodies to Angiotensin II", 1986, pp. 3365–3370.

Aston et al., "Monoclonal Antibodies to Human Growth Hormone Can Distinguish Between Pituitary and Genetically Engineered Forms", *Mol. Immunol.*, 22(3):271–275, 1985.

Krivi et al., "Antigenic Regions of Bovine Somatotropin as Defined by Monoclonal Antibodies", *Mol. Immunol.*, 23(12):1381–1389, 1986.

Seeburg et al., "Efficient Bacterial Expression of Bovine and Porcine Growth Hormones", *DNA*, 2(1):37–45, 1983.

Schoner et al., Biotechnology, 3, "Isolation and Purification of Protein Granules from *Escherichia coli* Cells Overproducing Bovine Growth Hormone", 1985, pp. 151–154.

Buell et al., Nucleic Acids Research, "Optimizing the Expression in *E. coli* of a Synthetic Gene Encoding Somatomedin-C (IGF-I)", 1985, pp. 1923–1938.

Motte et al., Clinica Chimica Acta., 174, "Construction and Clinical Validation of a Sensitive and Specific Assay for Serum Mature Calcitonin Using Monoclonal Anti-Peptide Antibodies", 1988, pp. 35–54.

Lasky et al., "Delineation of a Region of the Human Immunodeficiency Virus Type 1 gp120 Glycoprotein Critical for Interaction with the CD4 Receptor", *Cell*, 50:975–985, Sep. 11, 1987.

*Primary Examiner*—David L. Lacey
*Assistant Examiner*—Robert D. Budens
*Attorney, Agent, or Firm*—Wendell R. Guffey; Thomas L. Farquer

[57] ABSTRACT

Monoclonal antibodies are provided which differentiate between native and modified sequence proteins. Also provided are methods for using monoclonal antibodies to determine the relative amount of native and modified sequence proteins in a sample.

3 Claims, 1 Drawing Sheet

Fig.1
Phe-Pro-Ala-Met-Pro-Leu-Ser-Ser-Leu-Phe-Ala-Asn-Ala-Val-
               5                          10
Leu-Arg-Ala-Gln-His-Leu-His-Gln-Leu-Ala-Ala-Asp-Thr
  15              20                      25
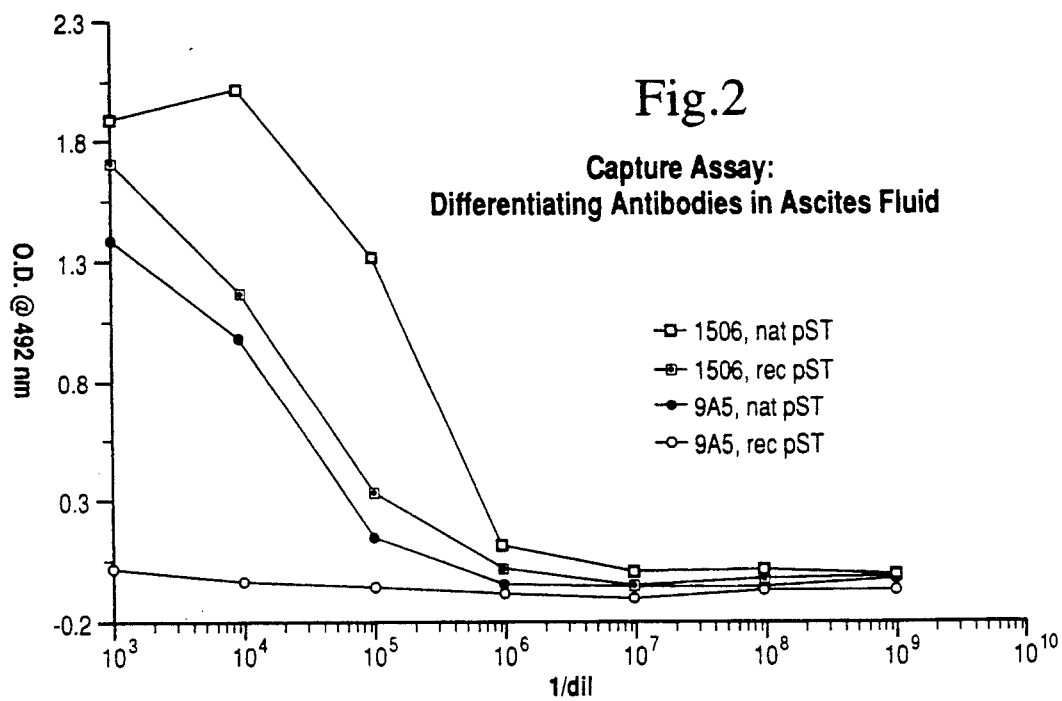
Fig.2
Capture Assay:
Differentiating Antibodies in Ascites Fluid
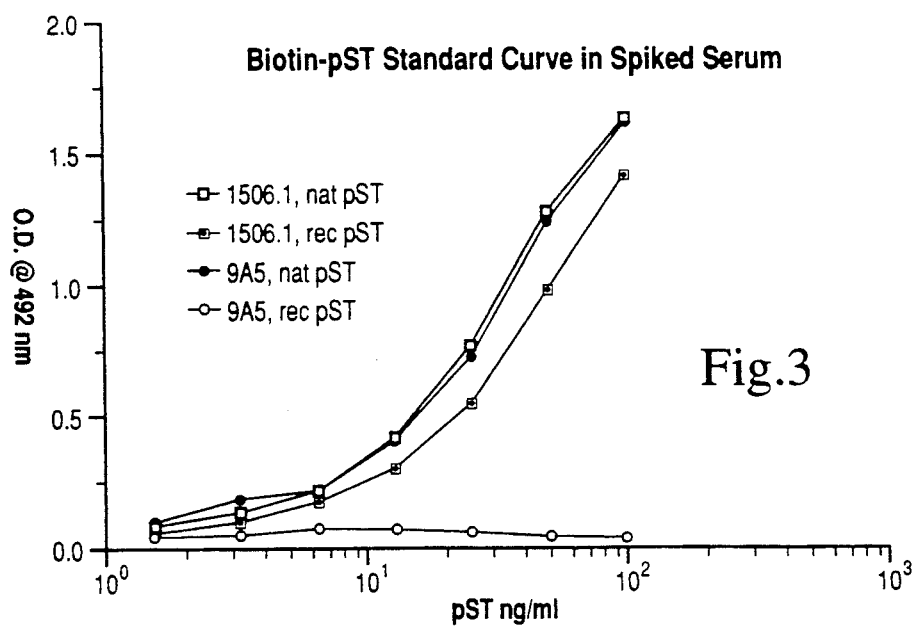
Fig.3

MONOCLONAL ANTIBODIES WHICH DIFFERENTIATE BETWEEN NATIVE AND MODIFIED PORCINE SOMATOTROPINS

This invention relates generally to monoclonal antibodies and particularly to monoclonal antibodies which differentiate between native and modified sequence proteins and methods for using such monoclonal antibodies to determine the relative amounts of native and modified sequence proteins in a sample.

BACKGROUND OF THE INVENTION

1. Recombinant Proteins

Methods for producing recombinant proteins are well known in the art; heterologous DNA segments that encode for a particular protein are inserted into host organisms using recombinant DNA technology. By growing the transformant organisms under conditions which induce the expression of proteins, heterologous proteins such as insulin, somatotropins, interleukins, interferons, somatomedins, and the like can be produced. For example, U.S. Pat. Nos. 4,604,359 and 4,332,717 disclose methods for producing human recombinant somatotropin; U.S. Pat. No. 4,431,739 discloses a method for producing recombinant somatotropins; E.P. Patent Application 0 104 920 discloses a method for producing recombinant porcine somatotropin; U.S. Pat. No. 4,443,539 discloses a method for producing recombinant bovine somatotropin; Schoner, *Biotechnology*, 3(2):151-54, discloses a method for producing recombinant somatotropin, and Buell, *Nucleic Acid Res.*, 13, 1923-38 (1985) discloses a method for producing recombinant somatomedin C.

Typically, the recombinant protein produced has an amino acid sequence which is the same as the amino acid sequence of the native protein.

Often, however, recombinant proteins produced using recombinant DNA techniques have an amino acid sequence which is not the same as the amino acid sequence of the native protein—a modified sequence protein.

It may be desirable to modify the amino acid sequence in a recombinant protein for several reasons. For example, a recombinant protein with a modified amino acid sequence may have physical or chemical properties which make it easier to recover the protein from the fermentation broth, refold and purify the protein during the recovery process, or formulate and administer the protein for the intended purpose. In addition, the modified sequence recombinant protein may have greater bioactivity than the native protein and cause less adverse side effects when administered for its intended purpose.

Also, when administering a modified sequence recombinant protein to an animal for its intended use, it is often difficult to distinguish between the native protein endogenous to the animal and the modified sequence protein administered to the animal. For example, when modified sequence somatotropin is administered to an animal to promote growth, the animal's serum can be assayed for total somatotropin levels using radioimmunoassay (RIA) or other well known techniques. However, it is difficult to differentiate between native and modified sequence somatotropin levels and determine if the modified sequence somatotropin is causing an increase in growth or if the increase in growth is caused by some factor which has increased native somatotropin levels.

Similarly, when somatotropin or any other endogenous protein is being delivered to an animal with a delivery device, it is difficult to determine if the modified sequence protein is being delivered to the animal in the required amounts or if all or part of the the protein can be attributed to endogenous protein.

Methods are, therefore, needed for differentiating between native and modified sequence proteins and for determining the relative amounts of native and modified sequence proteins, particularly modified sequence recombinant proteins, in a sample.

2. Protein Immunology

A macromolecular protein immunogen has several antigenic determinants. Immunizing an animal with a macromolecular protein results in the formation of different antibodies with different specificities for each antigenic determinant; the number of different antibodies depends on the number of antigenic determinants on the macromolecular protein and their inherent immunogenicity.

The immunogenicity of a particular antigenic determinant is dependent upon several factors including the amino acid sequence, conformation, segmental mobility, or hydropathicity of the antigenic determinant.

Antibodies, particularly monoclonal antibodies, formed in response to protein immunogens contain antigen combining sites that are highly specific for individual antigenic determinants on the protein. Thus, an antibody specific for a particular antigenic determinant of a protein will not react with that protein if the antigenic determinant has been deleted, modified or otherwise altered to change its immunogenicity.

When recombinant or synthetic proteins have an amino acid sequence which is not the same as the amino acid sequence of the native protein, the altered amino acids may affect the immunogenicity of an antigenic determinant containing the altered amino acid sequence.

3. Description of References

Pestka, U.S. Pat. No. 4,623,621, discloses the use of antibodies to distinguish monomeric from oligomeric forms of peptides and proteins. The assay employs a single monoclonal antibody in two different assay steps.

Sharp et al, U.S. Pat. No. 4,487,829, discloses the production and use of monoclonal antibodies against adenoviruses.

DESCRIPTION OF DRAWINGS

FIG. 1 shows the amino-terminus fragment of native somatotropin consisting of the first 27 amino acids.

FIG. 2 shows the results from a Capture Assay differentiating antibodies in Ascites Fluid.

FIG. 3 shows the results from an Assay of Biotin-pST in Spiked Serum.

SUMMARY OF THE INVENTION

It is, therefore, an object of the present invention to provide monoclonal antibodies which differentiate between native and modified sequence proteins.

It is another object of the present invention to provide monoclonal antibodies which differentiate between native and modified sequence somatotropins.

It is another object of the present invention to provide monoclonal antibodies which differentiate between native somatotropins and modified sequence somatotropins having deleted sequences.

It is another object of the present invention to provide monoclonal antibodies which differentiate between native somatotropins and modified sequence somatotropins having N-terminal deleted sequences.

It is a further object of the present invention to provide a method for determining the relative amount of native and modified sequence proteins in a sample.

It is another object of the present invention to provide a method for determining the relative amount of native and modified sequence somatotropins in a sample.

It is another object of the present invention to provide a method for determining the relative amount of native somatotropins and modified sequence somatotropins having deleted sequences in a sample.

It is another object of the present invention to provide a method for determining the relative amount of native somatotropins and modified sequence somatotropins having N-terminal deleted sequences in a sample.

These and other objects are achieved using monoclonal antibodies which differentiate between native and modified sequence proteins, preferably somatotropins. The monoclonal antibodies are native antibodies having an antigen combining site specific for a native antigenic determinant in the native protein. As such, the monoclonal antibodies will not react with modified sequence proteins which have had the native antigenic determinant deleted, modified or otherwise altered.

The monoclonal antibodies are formed by any acceptable method, preferably using the HAT selection technique well known to skilled artisans.

In the most preferred embodiment, monoclonal antibodies are provided which differentiate between native somatotropins and modified sequence somatotropins having N-terminal deleted sequences. The monoclonal antibodies are native antibodies having an antigen combining site specific for a native antigenic determinant located in about the first 1–40 amino acids on the N-terminal end of the native somatotropin. Monoclonal antibodies specific for native antigenic determinants located in the N-terminal 27 amino acids of porcine somatotropin have been produced; the hybridoma producing the antibodies has been deposited with The American Type Culture Collection (ATCC), Rockville, Md. and assigned Accession No. HB10308. Monoclonal antibodies produced by ATCC HB10308 will distinguish between native and N-terminal deleted sequence porcine somatotropins such as delta-7 porcine somatotropin.

Other objects, advantages, and novel features of the present invention will become apparent from the following detailed description of the invention.

DETAILED DESCRIPTION OF THE INVENTION

1. Definition of Terms

The term "modified sequence protein" is defined herein to mean a protein having bioactivity of a native protein but having an amino acid sequence different from the amino acid sequence of the native protein and includes synthetic proteins produced by chemical synthesis, transgenic animals, recombinant microorganisms and other suitable means. Modified sequence proteins may have an abbreviated amino acid sequence or an amino acid sequence similar to the native protein and their analogs and muteins having substituted, deleted, elongated, replaced, or otherwise modified sequences. In particular, modified sequence protein as used herein refers to a recombinant protein having the same amino acid sequence as the native protein but having amino acids deleted from the amino and/or carboxy terminal end.

The term "modified sequence somatotropin" is defined herein to mean a somatotropin having bioactivity of a native somatotropin but having an amino acid sequence different from the amino acid sequence of the native somatotropin and includes synthetic somatotropins produced by chemical synthesis and recombinant somatotropins produced by recombinant organisms. Modified sequence somatotropins may have an abbreviated amino acid sequence or an amino acid sequence similar to the native somatotropin and their analogs and muteins having substituted, deleted, elongated, replaced, or otherwise modified sequences. In particular, modified sequence somatotropin as used herein refers to a recombinant somatotropin having the same amino acid sequence as the native somatotropin but having amino acids deleted from the amino and/or carboxy terminal end. Examples of such proteins include but are not limited to delta-7 recombinant porcine somatotropin, delta-9 recombinant bovine somatotropin, (native somatotropins having 7 and 9 residues deleted from the amino terminal end, respectively), and the like.

The term "native antigenic determinant" is primarily defined herein to mean an amino acid sequence in the native protein which has been substituted, deleted, elongated, replaced, or otherwise modified to produce a modified sequence protein and a reasonable number of native amino acids surrounding the altered sequence which may be required to produce an antigenic determinant having the immunogenicity of the native protein. The term also includes an amino acid sequence in the native protein which has had its conformation and antigenicity changed by a modification in the protein in a location not in the sequence itself.

The term "native antibody" is defined herein to mean an antibody which has an antigenic combining site specific for the native antigenic determinant. The native antibody will, therefore, be specific for the native protein while not combining with the modified sequence protein.

2. The Invention

According to the present invention, monoclonal antibodies are provided which differentiate between native and modified sequence proteins. The monoclonal antibodies are native antibodies having an antigen combining site specific for the native antigenic determinant in the native protein; the monoclonal antibodies will not react with modified sequence proteins which have had the native antigenic determinant deleted, modified or otherwise altered.

The monoclonal antibodies and methods of the present invention can be used to differentiate between and determine the amount of any native and modified sequence protein which has a native antigenic determinant. These include but are not limited to somatotropins, prolactins, placental lactogens, somatomedins, somatostatins, insulins, interleukins, and the like.

The monoclonal antibodies of the present invention are formed by using the amino acid sequence of the native antigenic determinant as an immunogen. The immunogen is injected into an animal and immune spleen cells are isolated and fused with myelomas to produce hybridomas. A hybridoma which makes monoclonal antibody specific for the native antigenic determinant is isolated and used to make native antibodies which will combine with the native protein but will not combine with the modified sequence protein since the modified sequence has had the native antigenic determinant deleted, modified or otherwise altered.

Methods for making hybridomas which produce monoclonal antibodies from immune spleen cells and myelomas are well known in the art, particularly methods using the HAT (hypoxanthine, aminopterin, thymidine) selection technique.

The native antigenic determinant used as an immunogen is prepared by any suitable means, typically by synthesizing an amino acid sequence corresponding to the native protein amino acid sequence containing the amino acid sequence which has been altered to produce the modified sequence protein or by excising a section of a protein which has the immunogenicity of the native antigenic determinant. It may be necessary to include a number of amino acids on either side of the native antigenic determinant to produce an immunogen which will elicit an antibody response from the immune system of the injected animal or to maintain the desired characteristics of the native antigenic determinant. These additional amino acids may be part of the native amino acid sequence or may be necessary to elicit an immune response, particularly if the altered sequence is a hapten or if the additional amino acids are necessary to insure the conformation of the native antigenic determinant. It is sometimes necessary to insure the secondary structure of an antigenic determinant to elicit the proper antibody response.

In the preferred embodiment, monoclonal antibodies are provided which differentiate between native and modified sequence somatotropins. The monoclonal antibodies are native antibodies having an antigen combining site specific for the native antigenic determinant in the native somatotropin; the monoclonal antibodies will not react with modified sequence somatotropins which have had the native antigenic determinant deleted, modified or otherwise altered. The somatotropins useful in the present invention can be from any species but are preferably bovine, porcine, avian, ovine, piscine or subhuman somatotropin, most preferably porcine or bovine somatotropin.

In the most preferred embodiment, monoclonal antibodies are provided which differentiate between native somatotropins and modified sequence somatotropins having N-terminal deleted sequences. The monoclonal antibodies are native antibodies having an antigen combining site specific for a native antigenic determinant located in about the first 1–40 amino acids of the N-terminal end of the native somatotropin; the monoclonal antibodies will not react with modified sequence somatotropins which have had the N-terminal native antigenic determinant deleted, modified or otherwise altered.

Several somatotropins having an N-terminal native antigenic determinant modification are known in the art. European Patent Application Publication No. 0 103 395 describes the construction of a transformant strain of $E.$ $coli$ containing a first plasmid which codes for delta-9 (Ser) bovine somatotropin (somatotropin less its 9 N-terminal amino acids and having an additional serine residue at the N-terminus) under the control of the lambda $P_L$ promoter-operator which has a Shine-Dalgarno region derived from bacteriophage mu. The transformant also contains a second plasmid, pcI857, which codes for the production of the pcI857 temperature-sensitive repressor protein. The repressor protein can be inactivated by raising the temperature to about 42° C., thereby inducing expression of delta-9 (Ser) bovine somatotropin. A transformant strain of this type, $E.$ $coli$ HB101 ($P_L$-mu-delta-9 (Ser) bovine somatotropin and pcI857) has been deposited, with The American Type Culture Collection (ATCC), Rockville, Md. and assigned Accession No. 53030.

Construction of a similar transformant strain which codes for the production of delta-7 porcine somatotropin (porcine somatotropin less its first 7 N-terminal amino acids) is described in European Patent Application Publication No. 0 104 920. A transformant strain of this type, $E.$ $coli$ HB101 ($P_L$-mu-delta-7 porcine somatotropin and pcI857) has been deposited with ATCC and assigned Accession No. 53031.

Strains 53030 and 53031 are prolific producers of delta-9 (Ser) bovine somatotropin and delta-7 porcine somatotropin, respectively. Other methods for many similar proteins are known in the art.

Monoclonal antibodies specific for native antigenic determinants located in the N-terminal amino acids of porcine somatotropin have been produced; the hybridoma producing the antibodies has been deposited with The American Type Culture Collection (ATCC), Rockville, Md. and assigned Accession No. HB10308. Monoclonal antibodies produced by ATCC HB10308 will distinguish between native and N-terminal deleted sequence porcine somatotropins such as delta-7 porcine somatotropin.

According to the present invention, a method is provided for determining the relative amount of native and modified sequence proteins in a sample. The method comprises three steps: (1) determining the total amount of the native and modified sequence protein in the sample, (2) determining the amount of the native protein in the sample by reacting a native antibody having an antigen combining site specific for the native antigenic determinant in the native protein and determining the amount of native antibody-native protein complex formed by the reaction, and (3) calculating the amount of the modified sequence protein in the sample by subtracting the amount of the native protein in the sample from the total amount of the native and modified sequence protein in the sample.

The total amount of the native and modified sequence protein in the sample can be determined by means known to skilled artisans. Typical methods include but are not limited to radioimmunoassays, enzyme-linked immunosorbent assays, and the like.

The antibody-antigen reaction between the native antibody and the native protein is conveniently accomplished by mixing a sample containing the native protein with a complexing amount of the native antibody. The amount of native antibody reacted with the sample should be more than sufficient to form a complex with all the native protein in the sample (antibody should be present in excess). The amount will vary depending on the sample size, amount of native protein in the sample, and the like.

The amount of native antibody-native protein complex formed by the reaction can be determined by conventional means such as immumoprecipitation of the complex, color formation in enzyme-linked immunosorbent assays, and the like.

In the preferred embodiment, a method is provided for determining the relative amount of native and modified sequence somatotropins in a sample. The method comprises steps 1–3 as described above using samples containing native and modified sequence somatotropin and a native antibody having an antigen combining site specific for the native antigenic determinant in the native somatotropin.

More preferably, a method is provided for determining the relative amount of native somatotropin and modified sequence somatotropin having N-terminal deleted sequences in a sample. The method comprises steps 1-3 as described above using (1) samples containing native somatotropin and modified sequence somatotropin having N-terminal deleted sequences and (2) a native antibody having an antigen combining site specific for a native antigenic determinant located in about the first 1-40 amino acids of the N-terminal end of the native somatotropin. The native antibody is preferably a monoclonal antibody which will not react with modified sequence somatotropins which have had the N-terminal native antigenic determinant deleted, modified or otherwise altered.

Most preferably, the native antibody is a monoclonal antibody specific for native antigenic determinants located in the N-terminal amino acids of porcine somatotropin; the hybridoma producing the antibody has been deposited with The
Type Culture Collection (ATCC), Rockville, Md. and assigned Accession No. HB10308.

Also according to the present invention, a method is provided for determining the amount of modified sequence protein in a sample. The method comprises (1) reacting a native antibody having an antigen combining site specific for a native antigenic determinant in the native protein to form a native antibody-native protein complex, (2) separating the native antibody-native protein complex from the sample, and (3) determining the amount of the modified sequence protein in the sample.

The antibody-antigen reaction between the native antibody and the native protein is conveniently accomplished by mixing a sample containing the native protein with a complexing amount of the native antibody. The amount of native antibody reacted with the sample should be more than sufficient to form a complex with all the native protein in the sample. The amount will vary depending on the sample size, amount of native protein in the sample, and the like.

The native antibody-native protein complex can be removed from the sample by conventional means such as column chromatography, immunoprecipitation, high pressure liquid chromatography, and the like.

The amount of modified sequence protein in the sample can be determined by means known to skilled artisans. Typical methods include but are not limited to radioimmunoassays, enzyme-linked immunosorbent assays, and the like.

In the preferred embodiment, a method is provided for determining the amount of modified sequence somatotropin in a sample. The method comprises steps 1-3 as described above using samples containing native and modified sequence somatotropin and a native antibody having an antigen combining site specific for the native antigenic determinant in the native somatotropin.

Most preferably, a method is provided for determining the amount of modified sequence somatotropin having N-terminal deleted sequences in a sample. The method comprises steps 1-3 as described above using (1) samples containing native somatotropin and modified sequence somatotropin having N-terminal deleted sequences and (2) a native antibody having an antigen combining site specific for a native antigenic determinant located in about the first 1-40 amino acids of the N-terminal end of the native somatotropin. The native antibody is preferably a monoclonal antibody which will not react with modified sequence somatotropins which have had the N-terminal native antigenic determinant deleted, modified or otherwise altered.

Most preferably, the native antibody is a monoclonal antibody specific for native antigenic determinants located in the N-terminal 27 amino acids of porcine somatotropin; the hybridoma producing the antibody has been deposited with The American Type Culture Collection (ATCC), Rockville, Md. and assigned Accession No. HB10308.

The invention having been generally described, the following examples are given as particular embodiments of the invention and to demonstrate the practice and advantages thereof. It is understood that the examples are given by way of illustration and are not intended to limit the specification or the claims to follow in any manner. In particular, recombinant proteins used in the experiments were prepared from transformed E. Coli strains which produce delta-7 porcine somatotropin. The somatotropin was isolated from E. Coli host strain HB101 transformed with a first plasmid (pL-mu-delta-7 porcine somatotropin) coding for delta-7 porcine somatotropin and a second plasmid (pCI 857) coding for the temperature sensitive lambda phage repression protein. Many other strains of organisms produce many types of recombinant proteins which will function in the present invention.

EXAMPLE 1

An amino-terminus fragment consisting of the first 27 amino acids (N27) of native somatotropin, shown in FIG. 1, was synthesized for use as an immunogen using techniques well known in the art. This particular fragment size was chosen because it contains both the 7 amino acids which have been deleted from the amino-end of delta-7 recombinant porcine somatotropin and a complete alpha helix. Thus, this fragment was likely to structurally resemble the corresponding segment in the native porcine somatotropin, not only in the primary structure, but also in secondary and tertiary structure. In addition, a peptide of 27 amino acids would be immunogenic whereas a 7 amino acid sequence would be a hapten and require conjugation to a carrier to elicit an immune response.

EXAMPLE 2

Biotinylation of porcine somatotropin: Porcine somatotropin was added to carbonate buffer (pH 9.6) to a final concentration of 10 mg/ml. A 50 mg/ml solution of biotin ester was made by adding biotin-N-hydroxysuccinimide ester (Bethesda Research Laboratories) to dimethylformamide which had been stored over molecular sieves. The two solutions were combined in a reaction vial and stirred at room temperature for 1.5 hours. The reaction was stopped by the addition of 1M NH4Cl to a final concentration of 0.1M. The biotinylated porcine somatotropin was dialyzed against PBS (pH 7.6) 3 times over 2 days. The final porcine somatotropin concentration was determined by absorbance at 278 nm. Biotinylated porcine somatotropin was diluted 1:100 and stored frozen at −70° C.

EXAMPLE 3

Production of Hybridomas: Mice—Six to eight week old female Balb/c mice were obtained from Charles River Laboratories. For the duration of the studies, they were allowed food and water ad libitum.

Immunizations—For the primary immunizations, N27 was dissolved in carbonate buffer (pH 9.6) and then emulsified in Freund's complete adjuvant (Gibco). Mice were inoculated subcutaneously with 100 μg of N27 in 0.2 ml. Two to three weeks later, mice were boosted by intrapertioneal injection of 10 to 50 μg N27 in PBS. Subsequent boosts were given in a similar manner with a minimum interval of three weeks between boosts.

EXAMPLE 4

Preparation of SP2/0 cells for Fusion: SP2/0 cells (obtained from the American Type Culture Collection) were grown in Dulbecco's modified Eagle media (DMEM) containing 1500 mg glucose/liter (Gibco) supplemented with 10% fetal calf serum (Hyclone), 1 mM sodium pyruvate, 2 mM glutamine and 1% penicillin-streptomycin (all obtained from Gibco). Cells were subcultured at a ratio of 1:4 to 1:10 when confluent.

Three days preceding the cell fusion, cells were seeded at a concentration of $5 \times 10^4$ cells/ml which allowed the cells to enter log phase growth before the fusion.

EXAMPLE 5

Preparation of Spleen Cells for Fusion: Three days following a boost, the immunized mouse was sacrificed and the spleen was aseptically removed. The spleen was placed in a petri dish containing DMEM and the lymphocytes were gently teased out of the spleen with sterile forceps. Cells obtained in this manner were centrifuged at $160 \times g$ for 10 minutes. The spleen cell pellet was resuspended in DMEM and pelleted at $160 \times g$ for 5 minutes. This was repeated two times. An aliquot of spleen cells was removed and counted using a Coulter counter. Zapoglobin (Coulter Diagnostics) was used to lyse the red blood cells. Routinely, approximately $1 \times 10^8$ spleen node cells were obtained.

EXAMPLE 6

Fusion Protocol: Spleen cells were mixed with SP2/0 cells at a 4:1 ratio. The cell mixture was pelleted at $200 \times g$ for 5 minutes and the supernatant was carefully removed. One ml of PEG-1500 (American Type Culture Collection) and various volumes of growth media were added dropwise in the following sequence:

| Addition | Time |
| --- | --- |
| 1 ml PEG | 1 minute |
| Gently stir | 1 minute |
| 1 ml media | 1 minute |
| 1 ml media | 1 minute |
| 8 ml media, stirring | 2 minutes |

Touching the sides and bottom of the centrifuge tube with the pipette was avoided when stirring.

The cells were centrifuged at $200 \times g$ for 5 minutes and resuspended in approximately 53 ml of growth media. Cells were dispensed into 5 96-well plates (Costar) at 0.1 ml/well and incubated at 37° C. (5% carbon dioxide) overnight. 0.1 ml HAT (Sigma) medium (hypoxanthine, aminopterin, thymidine) was added to each well the next day. Cells were refed with HAT media twice a week for three weeks and then fed with HT (Sigma) medium (hypoxanthine, thymidine) for an additional two weeks. Afterwards, cells were maintained on standard growth media.

Ascites Fluids—Balb/c mice were injected intrapertioneally with 0.5 ml pristane (2, 6, 10, 14-tetramethyl pentadecane, Sigma). Ten days later mice were given $5 \times 10^5$ hybridoma cells i.p. using a 21 gauge needle. Swelling of the abdomen of the inoculated mouse was observed in 1-3 weeks. The ascites fluid was harvested by holding the mouse with the abdomen side up and inserting an 18 gauge needle with no syringe attached into the abdomen. The mouse was tilted to allow fluid to collect into a 15 ml centrifuge tube. Ascites fluid was centrifuged at $200 \times g$ for 15 minutes and the clarified fluid was removed and frozen for later use. Fluid was collected from a mouse on alternate days till the mouse succumbed to the tumor.

EXAMPLE 7

Evaluation of Hybridomas by ELISA: Miscellaneous Solutions: 10xPBS: 12.36 g $Na_2HPO_4$, 1.8 g $NaH_2PO_4$, 85 g NaCl. Add distilled water to make 1 liter. OPD substrate: 30 ml 0.2M $Na_2HPO_4$+25 ml 0.1M citric acid, correct to pH 5.0. Add 25 μg o-phenylenediamine (Sigma) and stir until dissolved. Add 40 μl 30% $H_2O_2$ (Sigma) just prior to use.

Colonies were assayed as early as two weeks after the fusion. Ninety-six-well ELISA plates (Nunc) were coated with 600 ng/well native porcine somatotropin overnight at 4° C. or for 4 hours at 37° C. Plates were washed three times using PBS+0.1% Tween-20 and blocked with 2% BSA in PBS for 1-2 hours at 37° C. or overnight at 4° C. Plates were then washed as before. One hundred (100) μl of fusion supernatants were added to the wells and allowed to incubate 3-4 hours at 37° C. Plates were washed and 100 μl of an appropriate dilution of horseradish peroxidase conjugated goat anti-mouse antibody (Cappel, Cat. #3211-0081) was added to each well. Plates were incubated for 2-4 hours at 37° C. and then washed. One hundred (100) μl well OPD substrate was added. A color change was observed within 20 minutes and the development stopped by addition of 50 μl well 12% sulfuric acid. Plates were read on an ELISA reader (Titertek Multiskan) using a filter with a wavelength of 492 nm. Wells positive to native porcine somatotropin were reassayed by ELISA on native and recombinant porcine somatotropin.

EXAMPLE 8

Capture Assays: These assays were used with either biotinylated porcine somatotropin or radiolabeled porcine somatotropin. Ninety-six-well plates made by Nunc were used in the biotin-pST assays. Flexible assay plates (Falcon 3911 Micro Test III) were used when using radiolabeled materials.

Ninety-six-well ELISA plates were coated with 2 μg/ml affinity purified goat anti-mouse immunoglobulin overnight at about 4° C. Plates were washed three times using PBS+ 0.1% Tween-20 and blocked with 2% BSA in PBS for 1-2 hours at 37° C. or overnight at 4° C. Plates were then washed as before. One hundred (100) μl/well of antibodies (supernatants or ascites fluids in appropriate dilutions) were added and incubated for 3-4 hours at 37° C. Plates were washed. One hundred (100) μl/well biotinylated porcine somatotropin or radiolabeled porcine somatotropin were added and allowed to bind for 2.5-3 hours at 37° C. Plates were washed.

When radiolabeled porcine somatotropin was used, wells from flexible plates were cut and individual wells placed into test tubes for counting on a gamma counter.

When biotinylated porcine somatotropin was used, one hundred (100) μl/well of an appropriate dilution of streptavidin-horseradish peroxidase conjugate (Bethesda Research Laboratories) was added and incubated at 37° C. for 30 minutes. Plates were washed thoroughly. One hundred (100) μl/well OPD substrate was added. Upon completion of color change, 50 μl/well of 12% sulfuric acid was added and the absorbance was quantified using a Titertek MultiSkan. Several wells were positive for pST and were chosen for cloning.

EXAMPLE 9

Cloning of Hybridomas: Cells in a desired well were carefully suspended. A small aliquot was removed and cells were counted using a hemocytometer. Cells were diluted to a concentration of 5 cells/ml in growth media containing 10% conditioned media. Cells were dispensed into 96 well trays at 0.2 ml/well. Plates were left undisturbed to allow growth of distinct colonies. Antibody production was evaluated by ELISA. Positive wells containing a single colony were picked and cells were further subcloned to determine their clonality. Desired cells which proved to be monoclonal were frozen for future use.

EXAMPLE 10

Monoclonal antibodies produced from N27-immunized mice are capable of differentiating between native and recombinant porcine somatotropin. In solid phase assays, supernatants bound specifically to native porcine somatotropin at dilutions below 1:4000 (Table 1), while ascites bound at dilutions less than 1:10$^6$ (Table 2). None of the monoclonal antibodies had significant binding towards recombinant porcine somatotropin in these assays.

EXAMPLE 11

Capture assays were performed to assess relative affinity of the monoclonal antibodies toward labeled porcine somatotropin in a liquid phase. In these assays, 9A5 ascites had a high affinity for native porcine somatotropin and no significant affinity for recombinant porcine somatotropin. An anti-pST positive control bound identically to both somatotropins (FIG. 2).

EXAMPLE 12

The ability to bind to labeled porcine somatotropin in porcine serum was assessed in capture assays where serum was "spiked" with porcine somatotropin conjugated to biotin. Significant binding was observed (FIG. 3). 9A5 Ascites bound to porcine somatotropin at concentrations as low as 6 ng/ml (0.6 ng/well). Detectability is similar to that obtained with radioimmunoassays.

Monoclonal antibodies specific to native but not recombinant porcine somatotropin were shown to bind in solid phase assays and liquid phase capture assays. The antibodies were able to bind to labeled porcine somatotropin in spiked serum at low concentrations. No binding was detected in unspiked samples.

The hybridoma producing the antibodies 9A5 was deposited with The American Type Culture Collection (ATCC), Rockville, Md. and assigned Accession No. HB10308.

TABLE 1

| 1/dil | Nat pST Mean | SD | Rec pST Mean | SD | Nat pST Mean | SD | Rec pST Mean | SD |
|---|---|---|---|---|---|---|---|---|
| | Positive Control | | | | 9A5 | | | |
| 4 | 2.25 | .30 | 2.18 | .33 | 1.81 | .03 | 0 | .06 |
| 16 | 2.73 | .23 | 2.71 | .26 | 2.77 | .01 | .18 | 0 |
| 64 | 2.46 | .36 | 1.27 | .14 | 3.10 | .46 | .20 | .04 |
| 256 | 1.49 | .25 | .56 | .04 | 2.45 | .08 | .20 | .04 |
| 1024 | 0.47 | .11 | .15 | 0 | .95 | .08 | .08 | .07 |
| 4096 | 0.18 | .01 | .06 | .15 | .40 | .03 | .25 | .04 |
| 16384 | 0.05 | 0 | .08 | .14 | .14 | .01 | .18 | .06 |
| | 5F1 | | | | 9C7 | | | |
| 4 | 1.80 | .05 | 0 | .03 | 0.28 | .29 | 0 | .03 |
| 16 | 2.73 | .05 | .16 | .10 | 2.14 | .03 | .13 | .06 |
| 64 | 2.83 | .10 | .18 | .08 | 1.34 | .14 | .23 | .11 |
| 256 | 1.96 | .08 | .22 | .12 | .53 | .02 | .23 | .11 |
| 1024 | .56 | .05 | .07 | .09 | .13 | .02 | .13 | .12 |
| 4096 | .28 | .03 | .23 | .11 | .13 | .01 | .19 | .05 |
| 16384 | .12 | .01 | .14 | .10 | .07 | .03 | .17 | .08 |
| | Negative Control | | | | | | | |
| 4 | 0 | .01 | 0 | .02 | | | | |
| 16 | .02 | 0 | .13 | .02 | | | | |
| 64 | .07 | 0 | .17 | .01 | | | | |
| 256 | .07 | .01 | .18 | .08 | | | | |
| 1024 | 0 | .01 | .09 | .06 | | | | |
| 4096 | .04 | .01 | .18 | 0 | | | | |
| 16384 | .07 | .05 | .15 | .02 | | | | |

SD = standard deviation

TABLE 2

| 1/dil | Nat pST Mean | SD | Rec pST Mean | SD | Nat pST Mean | SD | Rec pST Mean | SD |
|---|---|---|---|---|---|---|---|---|
| | Positive Control | | | | 9A5 | | | |
| $10^3$ | 1.78 | .06 | 1.48 | .32 | 1.85 | .03 | 0 | .1 |
| $10^4$ | 2.63 | .15 | 2.39 | 0.07 | 2.76 | .04 | .29 | .1 |
| $10^5$ | 1.60 | .62 | 1.05 | .12 | 2.41 | .04 | .15 | .03 |
| $10^6$ | 0.27 | .1 | 0.46 | .08 | 0.64 | .05 | .13 | .02 |
| $10^7$ | 0 | .02 | 0.10 | .07 | 0.09 | .02 | .17 | .1 |
| $10^8$ | 0.08 | .01 | 0.27 | .06 | 0.09 | .02 | .24 | .01 |
| $10^9$ | 0 | .02 | 0.16 | .03 | 0 | .01 | .11 | .07 |
| | 5F1 | | | | Negative Control | | | |
| $10^3$ | 1.94 | .05 | .14 | .03 | .76 | .04 | 0 | .05 |
| $10^4$ | 2.70 | .04 | .13 | .03 | .06 | .04 | .24 | .04 |
| $10^5$ | 1.73 | .16 | .26 | .05 | .08 | .05 | .11 | 0 |
| $10^6$ | 0.45 | .06 | .26 | .03 | .08 | .02 | .10 | .01 |
| $10^7$ | 0.08 | .07 | .15 | .10 | 0 | .02 | .12 | .14 |
| $10^8$ | 0.10 | .03 | .31 | .05 | .12 | .12 | .31 | 0 |
| $10^9$ | 0.01 | .01 | .19 | .11 | 0 | 0 | .19 | .16 |

SD = standard deviation

We claim:

1. A monoclonal antibody which differentiates between native and delta-7 porcine somatotropin.

2. The hybridoma having A.T.C.C. Accession No. HB10308, said hybridoma producing monoclonal antibodies which differentiate between native and delta-7 porcine somatotropins.

3. Monoclonal antibodies produced by the hybridoma having A.T.C.C. Accession No. HB10308, which differentiate between native and delta-7 porcine somatotropins.

* * * * *